United States Patent [19]

Van Royen et al.

[11] 4,060,416
[45] Nov. 29, 1977

[54] STABILIZATION OF FREE-RADICAL PHOTOSENSITIVE MATERIALS

[75] Inventors: Freddy Ghisleen Van Royen, Ranst; Ludovicus Maria Mertens, Borgerhout; Jozef Willy Van Den Houte, Berchem, all of Belgium

[73] Assignee: AGFA-GEVAERT N.V., Mortsel, Belgium

[21] Appl. No.: 723,179

[22] Filed: Sept. 14, 1976

[30] Foreign Application Priority Data

Sept. 16, 1975 United Kingdom ............... 38072/75

[51] Int. Cl.² .......................... G03C 1/52; G03C 5/24; G03C 1/48
[52] U.S. Cl. .................... 96/48 R; 96/76 R; 96/90 R; 96/90 PC
[58] Field of Search ................ 96/48 R, 76 R, 90 R, 96/90 PC, 77

[56] References Cited

U.S. PATENT DOCUMENTS

| | | | |
|---|---|---|---|
| 3,918,973 | 11/1975 | Mertens | 96/90 R |
| 3,941,598 | 3/1976 | Goethem et al. | 96/90 PC |

*Primary Examiner*—Won H. Louie, Jr.
*Attorney, Agent, or Firm*—William J. Daniel

[57] ABSTRACT

A photosensitive recording material, which comprises a support bearing a layer containing at least one photosensitve organic polyhalogen compound producing free radicals upon exposure to ultraviolet and/or visible light, a dye precursor, which by the action of said free radicals is capable of forming a dye, and a thermally activatable stabilizing substance within the scope of the following general formula:

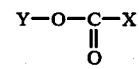

wherein:
X represents
1. an aryl group including a substituted aryl group, or
2. the group —OR¹ in which R¹ is an aryl group including a substituted aryl group,
3. the group —CH=CH—R² in which R² is an aryl group including a substituted aryl group, or
4. the group

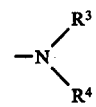

in which R³ stands for hydrogen, an alkyl group, or cycloalkyl group, an aryl group including a substituted aryl group and in which R⁴ stands for an alkyl group, a cycloalkyl group, or an aryl group including a substituted aryl group, or R³ and R⁴ together represent the necessary atoms to close a saturated nitrogen-containing heterocyclic ring, and
Y represents the group

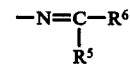

in which R⁵ represents hydrogen or an alkyl group, and R⁶ represents (1) an aryl group including a substituted aryl group or (2) an acyl group.

9 Claims, No Drawings

STABILIZATION OF FREE-RADICAL PHOTOSENSITIVE MATERIALS

The present invention is directed to a photosensitive recording material and method for forming a permanent or stabilized image resulting from the information-wise exposure of a free-radical photosensitive material as hereinafter defined, said method including the inactivation of the photosensitivity of the compound producing the free-radical.

By the term "free-radical photosensitive material" employed in the present description a photosensitive material is meant in which at least one of the ingredients is a photosensitive organic polyhalogen compound producing free radicals upon exposure to ultraviolet radiation and/or visible light. Said photosensitive material also comprises a colour modifier i.e. a dye precursor capable of showing a visible colour change by the action of said free radicals.

Photographic dye-forming systems based on the use of said polyhalogen compound and dye precursor compounds have been described e.g. in Phot. Sci. Eng. Vol. 5 No. 2 March–April (1961), J. Phot. Sci., 18 (1970), 33–37, in the U.S. Pat. Nos. 3,102,810, 3,147,117, 3,377,167, 3,525,616, and 3,558,317, the United Kingdom patent specification Nos. 1,065,548, 1,073,345, 1,076,368, and 1,151,578 and the Belgian Pat. Nos. 771,848, 786,973, 787,339, and 790,340 corresponding with the United Kingdom patent specification No. 1,359,472 and Applications 41,749/70, 40,349/71, 42,802/71, and 48,804/71 respectively.

In all these dye-forming systems carbon tetrabromide and/or iodoform are the most commonly used photoradical-generating compounds because they excel in photosensitivity when compared with other representatives of the class of photosensitive organic polyhalogen compounds.

One of the known stabilization techniques makes use of the volatility of carbon tetrabromide, which can be removed relatively easily from the non-exposed portions of the recording material by evaporation. A suitable stabilization temperature is in the range of e.g. 100° to 180° C.

The evaporation of carbon tetrabromide in the environment of the operating personnel, however, poses a problem since the compound is not physiologically inert and classified as being toxic (see I.Sax, Dangerous Properties of Industrial Materials (1968)).

The toxicity problem still remains when another commonly used stabilization technique is applied that is based on the extraction of the photosensitive polyhalogen compound.

In the known extraction-stabilization technique a solvent for the photosensitive polyhalogen compound is used, which solvent does not affect or only weakly affects the binding agent of the recording layer. Some solvents such as diethyl ether, although being excellent extraction agents, cannot be used because of the risk of explosion. Other suitable extraction solvents belonging to the class of liquid halogenated aliphatic hydrocarbons are immiscible with water and must not be drained off in the sewer.

Now a recording process has been found including image stabilization comprising the steps of:

1. image-wise exposing to active electromagnetic radiation a recording material containing in a recording layer a dye precursor compound and at least one photosensitive organic polyhalogen compound capable of producing photoradicals and a dyestuff with said dye precursor compound when exposed to ultraviolet radiation and/or visible light, and 2. heating the recording material, thereby converting the non-decomposed polyhalogen compound into a non-photosensitive substance with at least one thermally activatable stabilizing substance within the scope of the following general formula:

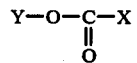

wherein:
X represents
1. an aryl group including a substituted aryl group, e.g. a phenyl group, or
2. the group $-OR^1$ in which $R^1$ is an aryl group including a substituted aryl group, e.g. a phenyl group or
3. the group $-CH=CH-R^2$ in which $R^2$ is an aryl group including a substituted aryl group, e.g. a phenyl group, or
4. the group

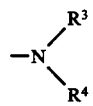

in which $R^3$ stands for hydrogen, an alkyl group or cycloalkyl group, an aryl group including a substituted aryl group e.g. a phenyl group, and $R^4$ stands for an alkyl group, a cycloalkyl group, or an aryl group including a substituted aryl group, or $R^3$ and $R^4$ together represent the necessary atoms to close a saturated nitrogen-containing heterocyclic ring, e.g. a pyrrolidine, piperidine, or morpholine ring, and Y represents the group

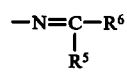

in which $R^5$ represents hydrogen or an alkyl group, e.g. a methyl group, and $R^6$ represents (1) an aryl group including a substituted aryl group, e.g. a phenyl group or alkoxy-substituted phenyl group, or (2) an acyl group, e.g. a benzoyl group.

The present invention includes a photosensitive recording material containing on a support the photosensitive organic polyhalogen compound and said thermally activatable stabilizing substance in admixture in the same layer. Said polyhalogen compound and stabilizing substance may, however, be present in separate layers e.g. adjacent layers with the proviso that the stabilizing substance can reach the organic polyhalogen compound when the recording material is heated.

As the above substances are substantially chemically inert at room temperature towards the photosensitive organic polyhalogen compound, there is no loss in photosensitivity when the recording material having the thermally activatable stabilizing substance and the polyhalogen compound in admixture in the same layer is stored.

It is assumed that the effective stabilizing substance is formed by thermal fission of the substances of the above general formula, thus setting free carbon dioxide. Of course, the scope of the invention is not restricted by this assumption.

Preferred recording materials of the present invention are those in which the said layer or layers containing the photosensitive organic polyhalogen compound, dye precursor compound, and/or the thermally activatable stabilizing substance are formed by a film-forming binder. A preferred binder is a N-vinylcarbazole homopolymer or copolymer.

The binder e.g. the N-vinylcarbazole polymer or copolymer film containing the above compounds and stabilizing substance may itself serve as a support, though preferably the recording composition is permanently supported by a separate heat-resistant film, in particular by a polyethylene terephthalate film.

The ratio by weight of N-vinylcarbazole polymer or copolymer to dye precursor compound in the recording layer may be in the range of about 20:1 to 2:1.

The photosensitive recording material according to the present invention preferably contains a spiropyran compound as dye precursor compound e.g. a spiropyran compound as described in the United Kingdom patent specification No. 1,359,472. Yet, the use of aromatic amines as dye precursor is not excluded. The ratio by weight of photosensitive organic polyhalogen compound to the dye precursor compound may be in the range of 1:1 to 1:50.

The recording material may contain fog-inhibiting compounds such as triphenyl-stibine, which is present in a weight ratio in respect of the photosensitive organic polyhalogen compound in the range of e.g., 1:100 to 2.5:100.

In a preferred recording material the photosensitive organic polyhalogen compound is carbon tetrabromide or a mixture of carbon tetrabromide and iodoform. These ultraviolet-sensitive compounds may be present in a binder such as poly-N-vinylcarbazole or polystyrene in a weight ratio ranging between 160:100 and 20:100.

In preferred recording materials the thermally activatable stabilizing substance is used in at least an equimolar amount with respect to the photosensitive organic polyhalogen compound, e.g. in a mole ratio range of 1:1 to 2:1.

The thermally activatable stabilizing agents may be used in conjunction with other stabilizing agents known to those skilled in the art for the same purpose, e.g. as described in the United Kingdom patent application Nos. 32,149/72 and 44,200/73 corresponding with Dt-OS Nos. 2,336,722 and 2,444,520 respectively.

The presence of a plasticizing agent in the recording material in the layer containing the photosensitive organic polyhalogen compound may improve the speed of stabilisation. Suitable plasticizing agents being compatible with a binder such as cellulose nitrate are e.g. polyalkylene glycol and camphor.

Particularly useful thermally activatable stabilizing agents are given in the following table together with their structural formula, melting point, and reference to their preparation description.

Table

| No. of compound | Structural formula | Melting point °C | Reference |
|---|---|---|---|
| 1 | (see figure) | 85 | Prep. 1 |
| 2 | (see figure) | 71 | Prep. 2 |
| 3 | (see figure) | 120 | Prep. 3 |
| 4 | (see figure) | 136 | Chem. Soc. 2169 (1923) |
| 5 | (see figure) | 130 | Prep. 4 |

Table-continued

| No. of compound | Structural formula | Melting point °C | Reference |
| --- | --- | --- | --- |
| 6 | ![structure] CO—O—N=CH—Ph with N-piperidine | 136 | Prep. 5 |
| 7 | ![structure] CO—O—N=HC—(2-OCH₃-Ph) with N-piperidine | 86 | Prep. 6 |

PREPARATION 1

6 g (0.05 mole) of benzaldoxime are dissolved in 100 ml of pyridine. The resulting solution is cooled down to 0° C with an ice-sodium chloride mixture. 18 g (0.06 mole) of 2,4-di-tert.pentylphenyl chloroformiate are added dropwise with stirring in 15 min. The temperature of the reaction mixture in the reagent bottle is kept between 0° and 10° C. A white precipitate forms and the reaction mixture, after having been stirred for 2.5 h more is allowed to stand overnight.

The reaction mixture is then poured into a mixture of 200 g of ice and 100 ml of water. An oily product separates, which upon further cooling and stirring becomes a yellow precipitate, which is sucked off.

The crude product is recrystallized from a mixture of 75 ml of methanol and 5 ml of water. Melting point of compound 1 : 85° C.

PREPARATION 2

An aqueous solution of 1N sodium hydroxide: 10 ml
1-phenyl-1,2-propanedione-2-oxime: 1.63 g
water: 10 ml
are introduced in a reaction flask of 100 ml carrying a dropping funnel.

The mixture is cooled down to 0° C and a solution of 1.7 g of cinnamic acid chloride in 10 ml of acetone is added dropwise with stirring. Stirring is continued for 2 h. An oily product separates, which is dissolved in ether. The crude product obtained after evaporation of the ether is recrystallized from methanol. Melting point of compound 2 : 71° C.

PREPARATION 3

A mixture of 2.4 g (0.02 mole) of benzaldoxime, 10 ml of ether and 5 ml of triethylamine is added dropwise to a solution of 3 g (0.02 mole) of 4-morpholinocarbonylchloride in 30 ml of ether. The reaction mixture is allowed to stand for 4 h. whereupon the ether is removed by evaporation. The solid residue is recrystallised from a mixture of ethanol and water. Melting point of compound 3 : 120° C.

PREPARATION 4

A mixture of 1 g of sodium hydroxide and 2.4 g of benzaldoxime in 10 ml of water is cooled down to 0° C.

2.6 g of 1-pyrrolidino-carbonylchloride are added dropwise with stirring and whilst maintaining the temperature between 0° and 10° C. The reaction mixture is extracted with ether. Compound 5 having a melting point of 130° C is obtained after evaporation of the ether.

PREPARATION 5

A solution of 1.47 g of 1-piperidinecarbonylchloride in 5 ml of ether is added dropwise to a mixture of 1.2 g (0.01 mole) of benzaldoxime, 10 ml of ether, and 2 ml of triethylamine.

The reaction mixture is allowed to stand for 1 h. The precipitate obtained is sucked off and washed with ether. Melting point of compound 6 : 136° C.

PREPARATION 6

3.7 g of 1-piperidinecarbonylchloride were added dropwise with stirring to a mixture of 1 g of sodium hydroxide and 3.7 g of 2-methoxybenzaldoxime in 25 ml of water, which has been cooled down to 0° C. Stirring is continued for 1 h. The precipitate formed is sucked off and washed with water. The crude product is recrystallized from a mixture of ethanol and water. Melting point of compound 7 : 86° C.

The stabilizing agents according to the above general formula, which are used very advantageously in conjunction with carbon tetrabromide, are also effective in the stabilisation of photo-sensitive materials containing photo-sensitive organic polyhalogen compounds other than carbon tetrabromide.

Photosensitive organic polyhalogen compounds that obtain reduced photosensitivity by reaction with the stabilizing agents referred to are within the scope of the following general formula that includes carbon tetrabromide:

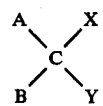

wherein:
each of A, B, X and Y is a halogen atom of the group of chlorine, bromine, or iodine, or wherein one of said substituents A, B, X, or Y represents an alkyl group including a substituted alkyl group, e.g. a halogen-substituted alkyl group, a hydroxyalkyl group, or an aralkyl group, e.g. benzyl, a quinoxaline group, an aryl group, a substituted aryl group, an aroyl group, or an arylsulphonyl group and the other substituents chlorine, bromine, or iodine, or wherein two of said substituents A, B, X, or Y represent an aromatic acyl group, e.g. benzoyl, and the other substituents chlorine, bromine or iodine.

Particularly suitable representatives within the scope of this general formula are organic halides such as carbon tetrabromide, bromoform, iodoform, hexachloroethane, hexabromoethane, pentabromoethane, 1,1,2,2-tetrabromoethane, α,α,α-tribromoacetophenone, α,αλ,α-tribromomethylsulphonylbenzene, and its chlorine- or nitro-substituted derivatives, tribromoethanol, and the 2-tribromomethylquinoxaline compounds described in Belgian Pat. No. 757,145.

The following examples illustrate the present invention without, however, limiting it thereto. The parts, percentages and ratios are by weight, unless otherwise indicated.

EXAMPLE 1

24 parts of carbon tetrabromide, 24 parts of iodoform, 24 parts of 3-methyl-di-β-naphthospiropyran, 30 parts of compound 1 of the table, 100 parts of poly-N-vinylcarbazole, 2 parts of silicone oil dissolved in 1446 parts of trichloroethylene and 1336 parts of methylene chloride were used for coating a photosensitive layer on a polyethylene terephthalate support at a coverage of 95 ml per sq.m.

After having been dried, the recording material was image-wise exposed for 20 sec. to ultraviolet radiation in an Actina SH (trade name) diazo copier containing an UV lamp of 1000 W and heated for 60 sec. at 140° C.

In the image background areas no colouration was detected even after an exposure of several days to normal daylight.

EXAMPLES 2-7

In the recording materials of said Examples 2-7 the following compounds were used in the amounts given instead of 30 parts of compound 1:
30 parts of compound 2 (Example 2)
40 parts of compound 3 (Example 3)
40 parts of compound 4 (Example 4)
30 parts of compound 5 (Example 5)
30 parts of compound 6 (Example 6)
30 parts of compound 7 (Example 7)

The same good image stability as that obtained in the recording material of Example 1 was obtained in all these recording materials.

EXAMPLE 8

Example 1 was repeated with the difference, however, that 48 parts of carbon tetrabromide were used instead of the mixture of 24 parts of carbon tetrabromide and 24 parts of iodoform.

Practically the same results were obtained.

We claim:
1. A photosensitive recording material, which comprises a support bearing at least one layer containing at least one photosensitive organic polyhalogen compound producing free radicals upon exposure to ultraviolet and/or visible light, a dye precursor in said layer or in a layer adjacent thereto, which by the action of said free radicals forms a dye, and a thermally activatable stabilizing substance within the scope of the following general formula:

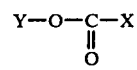

wherein:
X represents
 1. an aryl group,
 2. the group —OR$^1$ in which R$^1$ is an aryl group,
 3. the group —CH=CH—R$^2$ in which R$^2$ is an aryl group, or
 4. the group

in which R$^3$ stands for hydrogen, an alkyl group, a cycloalkyl group, an aryl group and in which R$^4$ stands for an alkyl group, a cycloalkyl group, or an aryl group, or R$^3$ and R$^4$ together represent the necessary atoms to close a saturated 5- or 6-membered nitrogen-containing heterocyclic ring, and
Y represents the group

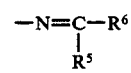

in which R$^5$ represents hydrogen or an alkyl group, and R$^6$ represents (1) an aryl group or (2) an acyl group.

2. A material according to claim 1, wherein the said thermally activatable stabilizing substance is present in a layer adjacent to the layer containing the organic polyhalogen compound, from which it can reach said compound upon heating of the material.

3. A material according to claim 1, wherein carbon tetrabromide or a mixture of carbon tetrabromide and iodoform is present as said photosensitive organic polyhalogen compound.

4. A material according to claim 1, wherein each such layer are formed by a film-forming binder.

5. A material according to claim 4, wherein the binder is a N-vinyl carbazole homopolymer or copolymer.

6. A material according to claim 1, wherein the thermally activatable stabilizing substance is used in at least an equimolar amount with respect to the photosensitive organic polyhalogen compound.

7. A material according to claim 6, wherein the thermally activatable stabilizing substance is used with respect to the organic polyhalogen compound in a molar range of 1:1 to 2:1.

8. A material according to claim 1, wherein the dye precursor is a spiropyran compound.

9. A recording process including image stabilization comprising the steps of:
 1. image-wise exposing to ultraviolet radiation and/or visible light a photosensitive recording material, which comprises at least one supported or self-supporting layer containing at least one photosensitive organic polyhalogen compound producing free radicals upon exposure to ultraviolet radiation and/or visible light, a dye precursor in said layer or in a layer adjacent thereto, which by the action of said free radicals forms a dye in the said layer or in a layer adjacent thereto, and a thermally activatable stabilizing substance within the scope of the following general formula:

$$Y-O-\underset{\underset{O}{\|}}{C}-X$$

wherein:

X represents 1. an aryl group,
2. the group —OR$^1$ in which R$^1$ is an aryl group,
3. the group —CH=CH—R$^2$ in which R$^2$ is an aryl group, or
4. the group

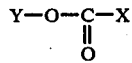

in which R$^3$ stands for hydrogen, an alkyl group, a cycloalkyl group or an aryl group and in which R$^4$ stands for an alkyl group, a cycloalkyl group or an aryl group, or R$^3$ and R$^4$ together represent the necessary atoms to close a 5- or 6-membered saturated nitrogen-containing heterocyclic ring, and Y represents the group

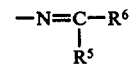

in which R$^5$ represents hydrogen or an alkyl group, and R$^6$ represents an aryl group, or an acyl group, and 2. heating the photo-exposed material to effect conversion of non-decomposed polyhalogen compound into a non-photosensitive condition by means of said thermally activatable substance.

* * * * *